United States Patent [19]

De Silva et al.

[11] Patent Number: 5,256,374
[45] Date of Patent: Oct. 26, 1993

[54] SAMPLE INTRODUCTION FOR SPECTROMETERS

[75] Inventors: K. Nimalasiri De Silva; Roger Guevremont, both of Ottawa, Canada

[73] Assignee: Her Majesty the Queen in right of Canada, as represented by the Minister of Energy Mines and Resources, Ottawa, Canada

[21] Appl. No.: 677,095

[22] Filed: Mar. 29, 1991

[30] Foreign Application Priority Data

Apr. 4, 1990 [CA] Canada .................................. 2013789

[51] Int. Cl.⁵ .............................................. G01N 31/12
[52] U.S. Cl. ........................................ 422/80; 422/67; 436/50; 436/52; 436/155; 436/181; 73/864.81; 250/288
[58] Field of Search .................... 422/63, 67, 68.1, 80, 422/103, 70; 436/52, 181, 50, 155, 171; 250/288; 73/864.81

[56] References Cited

U.S. PATENT DOCUMENTS

| 3,847,554 | 11/1974 | Su ..................................... 436/181 X |
| 4,268,478 | 5/1981 | Huber .............................. 436/181 X |
| 4,273,742 | 6/1981 | Huber et al. ............................ 422/80 |
| 4,344,917 | 8/1982 | Schorno ......................... 422/103 X |
| 4,740,356 | 4/1988 | Huber ............................... 422/80 X |
| 4,824,790 | 4/1989 | Carangelo et al. ............. 436/155 X |
| 4,836,039 | 6/1989 | De Silva .......................... 73/864.81 |
| 4,914,037 | 4/1990 | Forster et al. ..................... 422/80 X |

FOREIGN PATENT DOCUMENTS 2158608A 11/1985 United Kingdom .................. 422/63

Primary Examiner—James C. Housel
Assistant Examiner—Maureen M. Wallenhorst
Attorney, Agent, or Firm—Ronald G. Bitner

[57] ABSTRACT

A system for introducing a sample to an analyzing device, such as a spectrometer, wherein the flow rate of gas to the analyzing device is maintained substantially constant and uncontaminated during sample changeover. The system includes a flow controller and flow control paths arranged to avoid having any flow diverting valves or direction change in the analyte flow path.

6 Claims, 3 Drawing Sheets

SAMPLE INTRODUCTION FOR SPECTROMETERS

FIELD OF THE INVENTION

This invention relates to a system for introducing a sample to an analyzing device.

DESCRIPTION OF THE RELATED ART

In atomic spectrometry, the samples to be analyzed, which may be in the form of liquid aerosols, gas suspended solid particles, or vapours, are transported to the atomization source by means of a suitable carrier gas. One common system is Inductively Coupled Argon Plasma (ICP) Spectrometry. For convenience of operation of such a device and to obtain reproducibility of results, it is necessary to avoid interruptions from one sample to the next. Except for continuous flow nebulization of liquids, the sampling device must be opened and exposed to the atmosphere in order to change samples. While changing samples, it is desirable not to have the continuously flowing carrier gas contaminated with air as this can extinguish the plasma. To avoid this problem requires isolation of the gases entering the plasma from the gases inside the sample chamber during sample changeover. Commercially available, or other disclosed systems, for example, electrothermal vaporizers and laser ablation devices, consist of mechanical flow-diverting or shut-off valves in the analyte flow path in order to isolate the sample chamber from the plasma during the sample changeover. Having flow diverting valves in the analyte flow path causes turbulence and other problems associated with trapping of the analyte along the flow path resulting in analyte loss, memory effects (sample carry over from one sample to the other), and mechanical failure.

To facilitate obtaining reproducible results it is desirable that the conditions of the plasma be maintained unaltered from one sample run to the next, particularly with auto-tuned plasma sources which may not return to the original conditions if the operating conditions are changed. Specifically, it is desirable that the net gas flow rate to the spectrometer remain substantially constant during the operation and particularly during the period of sample changeover.

Also, during the period of sample changeover, the open sample chamber is susceptible to contamination from ambient air. Hence, it would be desirable to provide simple means for preventing contamination of the opened sample chamber.

It would also be desirable to provide a sample introduction system that is simple to automate or to operate unattended.

SUMMARY OF THE INVENTION

An object of the present invention is to provide a sample introduction system that avoids the requirement for flow diverting valves in the analyte flow path.

Another object of the present invention is to provide a sample introduction system that allows providing substantially constant gas flow rate to the plasma while samples are changed.

Another object is to provide a sample introduction system that allows a smooth straight flow path for the sample with reduced tendency of the sample to contact the walls of the passageway in the flow path.

Another object is to provide a sample introduction system that facilitates avoiding contamination of the opened sample chamber while changing samples.

Another object is to allow pre-processing of the sample during which time the undesired components can be diverted away from the analyzing device.

Another object is to allow manipulation of signal strength and duration without changing the total gas flow to the analyzing device.

Yet another object is to provide a sample introduction system that facilitates automation.

It has been found that the above objects can be met by a sample introduction system comprising: an openable sample chamber for receiving a sample; means for atomizing the sample; a flow combining portion connected with the outlet of the sample chamber, said flow combining portion having an inlet for receiving a carrier gas and an outlet for connection to an analyzing device; means for transporting the sample to the analyzing device; and flow control means for increasing the input of the carrier gas when the sample chamber is opened, such that the flow rate of gas to the analyzing device is maintained substantially constant while a portion of the carrier gas flows back through the outlet of the sample chamber to purge ambient air, said flow control means being disposed external to the flow path of the sample.

The term "atomizing" as used herein refers to the formation of an aerosol from a liquid or the breaking up of a particulate sample sufficiently to be readily carried by a gas, or the heating of a liquid or solid sample sufficiently to be vaporized.

DESCRIPTION OF THE PREFERRED EMBODIMENTS

Figure 1:
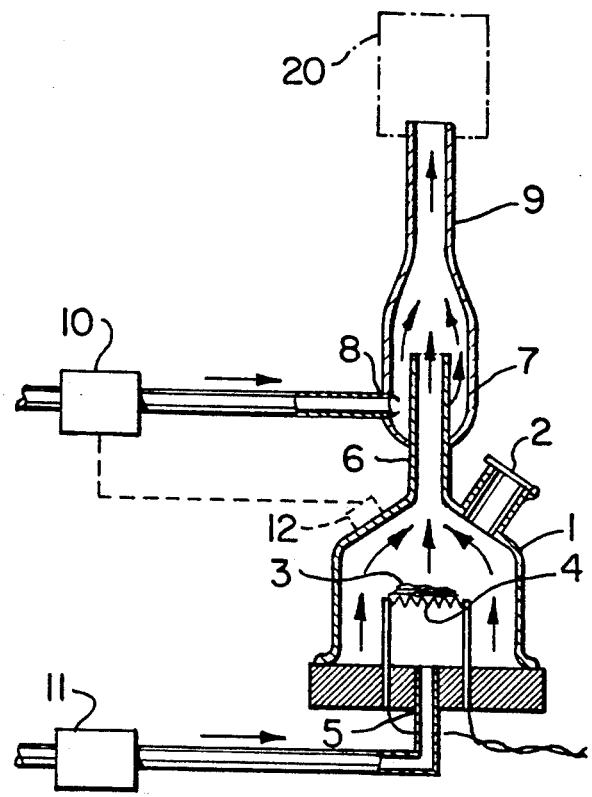
FIG. 1 is a schematic representation of one embodiment of the present invention shown operating with an electrothermal vaporizer.
Figure 2:
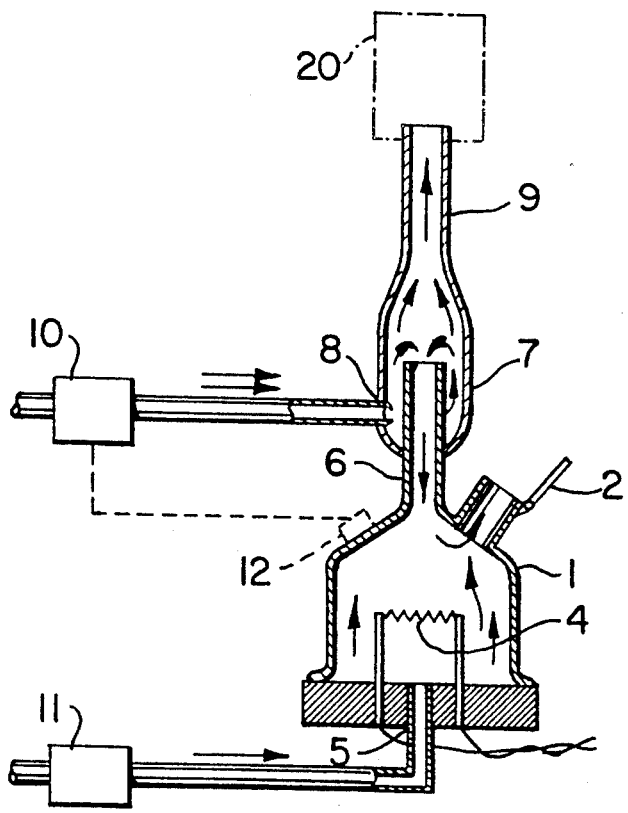
FIG. 2 shows the embodiment of FIG. 1 with the sample chamber opened for sample changeover.

Referring to FIGS. 1 and 2, the system of the present invention comprises a sample chamber 1 with access means, shown in the form of openable closure means 2, for receiving a sample 3 that is to be atomized by known heater means 4 for delivery to an analyzing device 20. The sample chamber 1 is provided with an inlet 5 for a gas and an outlet 6 for the gas and atomized sample. The gas supplied to inlet 5, referred to herein as the "sampler gas", provides the means for transporting the atomized sample from the chamber 1.

Connected to the outlet 6 of the sample chamber 1 is a flow combining portion 7 having an inlet 8 for receiving a gas, referred to herein as the "carrier gas", and an outlet 9 for connection to the analyzing device 20. The carrier gas transports the atomised sample to the analyzing device 20. The supply of the carrier gas is controlled by suitable flow control means 10.

Preferably the flow combining portion 7 defines an outer annular passageway surrounding the upper portion of the outlet 6 such that the carrier gas exits the outlet of the flow combining portion 7 in the form of a sheath about the atomized sample and sampler gas, to reduce the contact of the sample with the walls of the passageways in the flow path. To further reduce the likelihood of the sample contacting and adhering to the walls of the passageways in the flow path, the inlet 8 will preferably be connected tangentially to the flow combining portion 7 to provide spiral flow of the carrier gas within the flow combining portion 7 and through outlet 9 to the analyzing device 20.

Figure 3:
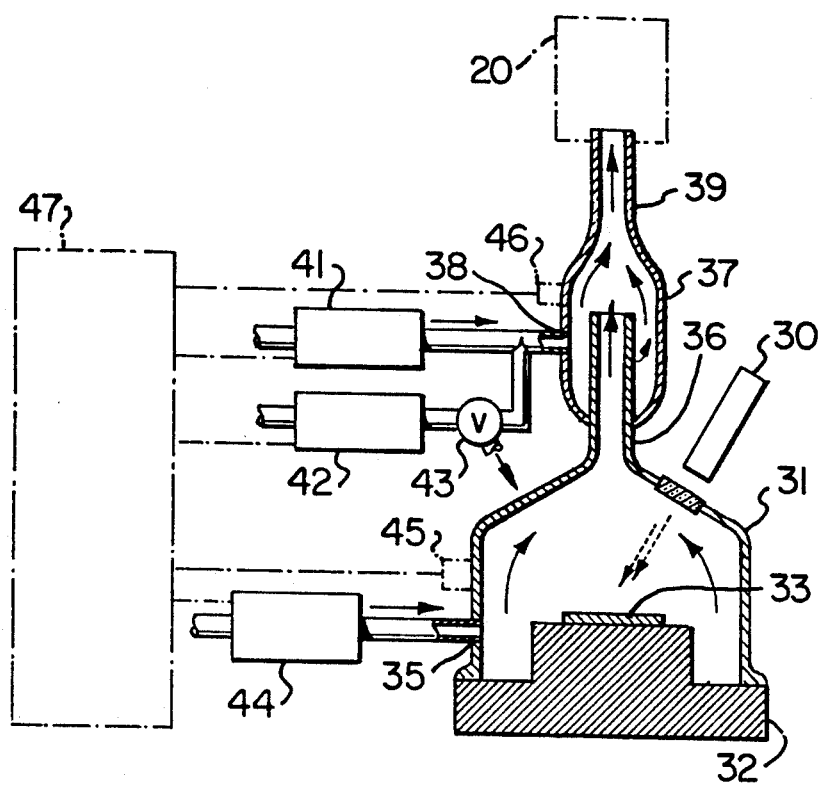
FIG. 3 is a schematic representation of an embodiment of the invention adapted for laser ablation.
Figure 4:
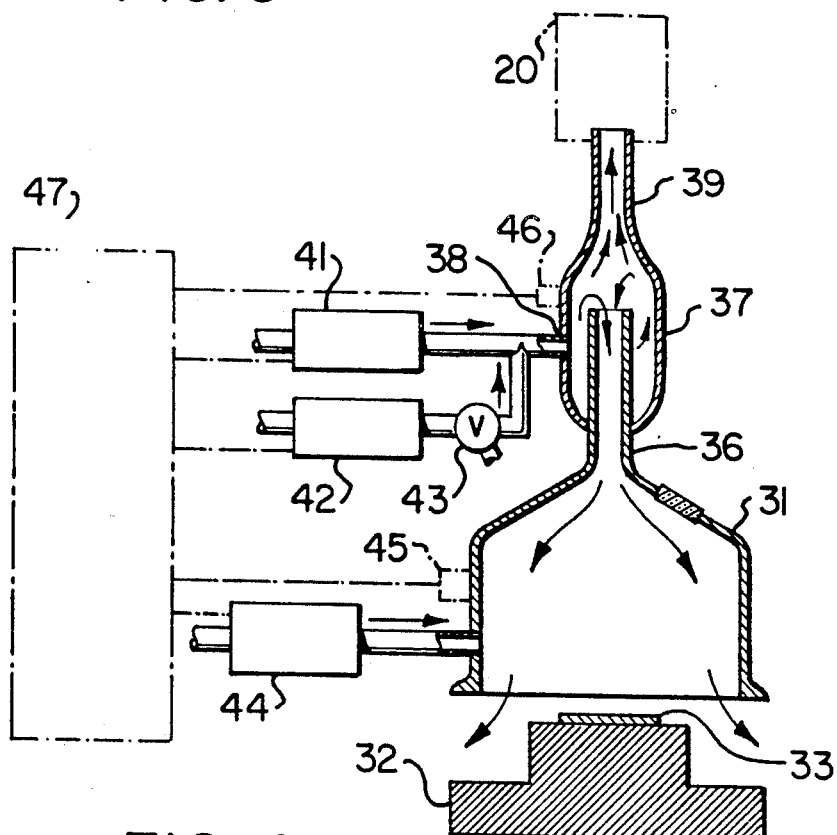
FIG. 4 shows the embodiment of FIG. 3 with the sample chamber open for sample changeover.
Figure 5:
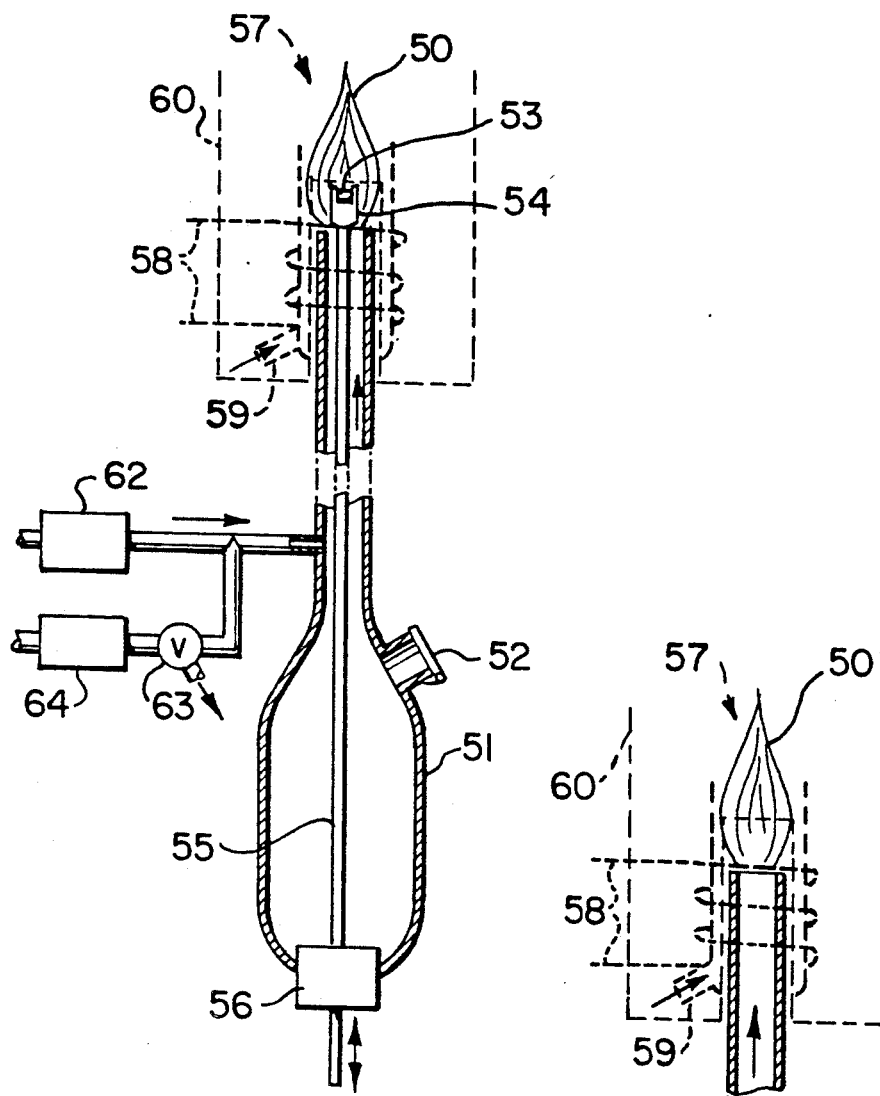
FIG. 5 is a schematic representation of an embodiment of the invention adapted for a direct sample insertion device.
Figure 6:
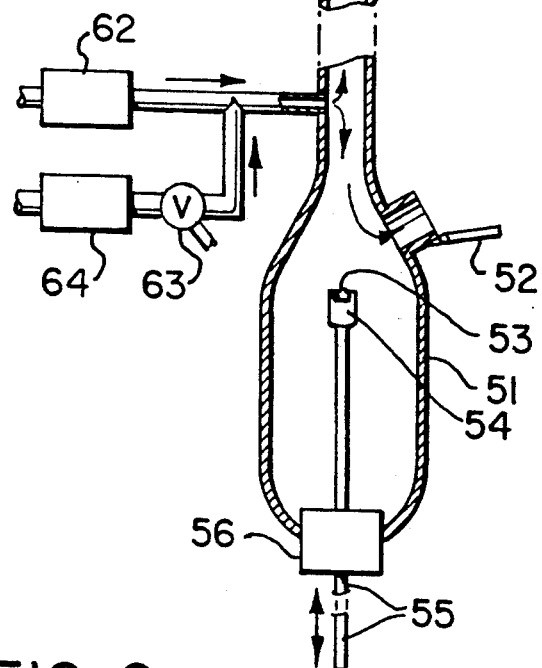
FIG. 6 shows the embodiment of FIG. 5 opened and positioned for sample changeover.

FIG. 1 shows the system in operation for transporting the atomized sample 3 with carrier gas to the analyzing device 20. The total gas flow to the analyzing device 20 comprises the sum of the gas flow rate of the sampler gas supplied to inlet 5, the carrier gas supplied to inlet 8, plus the flow rate of atomized sample. The flow rate of sample vapour is dependent on the volatility of the sample and the temperature of the heating means 4. The sampler gas can be supplied to inlet 5 at a relatively low rate sufficient to transport the atomized sample from the sample chamber 1. However, the transport rate can be chosen to provide the desired signal strength and duration. The sampler gas is shown controlled by a gas flow controller 11. The balance of the flow is provided by the carrier gas via inlet 8, controlled by gas controller 10, sufficient to provide the desired gas flow rate to the analyzing device. By having two separate controllers 10 and 11 the signal strength and duration, or proportions of flows, can be controlled for optimum performance.

The flow controller 10 operates to provide two flow rates of the carrier gas, one rate when the sample chamber 1 is closed as shown in FIG. 1, and another higher rate when the sample chamber is opened, as shown in FIG. 2, so that the gas flow rate to the outlet 9 and the analyzing device 20 is maintained substantially constant.

The operation of controller 10 can be automated with the use of pressure sensor 12. For example, the controller 10 can be made responsive to a predetermined drop in chamber pressure, indicative of the opening of the chamber 1, to provide gas flow at the required higher gas flow rate.

FIG. 2 shows the system during sample changeover. At this point the closure 2 is opened allowing a portion of the flow supplied at inlets 5 and 8 to escape. At the same time that the closure 2 is opened, the flow to inlet 8 is increased to the extent required to provide that the resulting flow to the analyzing device 20 remains substantially the same.

The portion of flow that exits from the closure 2, while open, serves to prevent contaminating ambient air from entering the sample chamber 1. Also, at this stage the flow system can be used to pre-process the sample (e.g. ashing the organic matter, vaporizing solvents, etc.) so that undesired gases or vapors exit via closure 2 and therefore do not enter the analyzing device.

FIGS. 3 and 4 show the invention adapted for laser ablation of sample 33 by means of laser 30. The system is basically similar to that shown in FIG. 1, comprising an openable sample chamber 31 with inlet 35 for a sampler gas and an outlet 36 for the sampler gas and atomized sample, the outlet 36 being connected with a flow combining portion 37 having an inlet 38 for a carrier gas and an outlet 39 for connection to an analyzing device 20. Access to the chamber 31 for sample changing is shown provided by a separable portion 32.

The flow rate of the carrier gas to inlet 38 is controlled by gas controllers 41 and 42, and diverter valve 43. The use of a diverter valve 43 facilitates allowing the controller 42 to maintain the desired stabilized flow for when it is required. Specifically, the gas flow into inlet 38 can be rapidly stepped from low to high flow with minimal stabilization time when the chamber 31 is opened as shown in FIG. 4.

While the chamber is opened, the portion of the flow that flows back through the outlet 36 serves to flush the chamber 31 of ambient air.

The gas flow controllers referred to herein may be in the form of mass controllers, or may control volume of flow.

In operation, with reference to FIGS. 3 and 4, while sample 33 is atomized by means of laser 30, a predetermined flow rate of sampler gas is provided to inlet 35. The atomized sample is carried by the sampler gas to the flow combining portion 37. For sample introduction, diverter valve 43 is set to divert the flow supplied via controller 42 so that the total carrier gas to combining portion 37 is supplied solely through controller 41. The combined flow rate of the sampler gas and carrier gas plus the atomized sample define the total flow rate to the analyzing device 20.

With reference to FIG. 4, when the sample chamber 31 is opened for sample changing, flow through valve 43 is directed to inlet 38 along with flow through controller 41. The additional gas flow rate provided by controller 42 is chosen such that the flow lost while the chamber 31 is opened is compensated for and the total flow rate to the analyzing device remains substantially the same. With the chamber 31 opened, as shown in FIG. 4, a portion of the gas flows from the chamber 31 and prevents ambient air from entering chamber 31 and purges any residual gases therein.

FIGS. 5 and 6 illustrate the present invention used with a direct sample insertion device, which as in previous embodiments comprises a chamber 51 with opening means 52. The sample 53 is placed on a suitable support member 54, which can be a graphite cup or a wire loop made of a refractory material. The support member 54 is mounted on a movable rod 55, which can be raised and lowered by suitable means such as a stepper motor 56. FIG. 5 shows the support member 54 raised into the analyzing device 60 whereby the sample is vaporized and atomized using the thermal energy of the inductively coupled plasma 50. During this time the access opening 52 will be closed and valve 63 will be closed. FIG. 6 shows the chamber 51 opened and the support member 54 lowered for sample changing. At this time the valve 63 is open to provide the additional flow from controller 64 that compensates for the flow lost through the opening 52, similar to that as described above with reference to the embodiments of FIGS. 1 to 4.

It should be noted that the embodiment of FIGS. 5 and 6 uses the components 54, 55 and 56 to provide the means of transporting the sample to the analyzing device 60, replacing the sampler gas of the embodiment of FIGS. 1 to 4. It should also be noted that the means for atomizing the sample, in this embodiment, is the plasma flame 50 generated by the inductively coupled plasma (ICP) torch 57 which also forms part of the analyzing device 60. As shown, the ICP torch includes an inductive load coil 58 and inlet 59 for coolant flow.

It will be understood that the systems described above can be automated. The acquisition of data from the sensors and the operation of the controllers, and any other adjustable components, may be controlled by the central processing unit 47. For example, with reference to FIGS. 3 and 4, valve 43 can be activated in response to a sensor, such as a pressure sensor 45, that detects the opening of the sample chamber 31. Alternatively, or in addition, a pressure sensor 46 may be provided in the combining portion 37, which can be used to control valve 43, and optionally controller 42, in order to maintain constant gas flow to the analyzing device 20.

It should be noted that with the present invention, there is no requirement for flow diverting valves in the analyte flow path. As can be seen in all embodiments described above, all control means, including diverter valves and controllers, are external to the flow path of the sample. This arrangement also facilities providing a smooth straight flow path for the sample with reduced tendency of the sample to contact the walls of the passageway in the flow path.

It will be understood that various modifications could be made to the embodiments described and that the flow control system of the present invention can be interfaced with other sample introduction devices and analyzing devices.

What is claimed is:

1. A system for introducing a sample to an analyzing device comprising:
    a sample chamber having openable access means for receiving a sample, said sample chamber also having an inlet and outlet;
    means for atomizing the sample within the sample chamber;
    a flow combining portion connected with the outlet of the sample chamber, said flow combining portion further having an inlet for receiving a carrier gas and an outlet for connection to an analyzing device;
    sampler gas supply means connected with the inlet of the sample chamber for transporting the sample from the sample chamber through the flow combining portion and to the analyzing device; and
    flow control means responsive to the opening of the access means of the sample chamber for increasing the input of the carrier gas to the flow combining portion when the access means of the sample chamber is opened, such that the flow rate of gas to the analyzing device is maintained substantially constant while a portion of the carrier gas flows back through the outlet of the sample chamber to purge ambient air, said flow control means being disposed external to the flow path of the sample extending from the sample chamber to the analyzing device.

2. The system of claim 1 wherein the flow control means comprises a first gas controller providing a continuous substantially constant basal flow rate of carrier gas, and a second gas controller providing an additional gas flow rate of carrier gas corresponding to the flow lost while the access means of the sample chamber is open.

3. The system of claim 2 wherein the flow control means further comprises a gas controller for controlling the flow rate of sampler gas.

4. The system of claim 1 wherein the flow combining portion comprises an outer annular passageway for the carrier gas surrounding an upper portion of the outlet of the sample chamber such that the carrier gas exits the outlet of the flow combining portion in the form of a sheath about the sample and sampler gas.

5. The system of claim 1 wherein the flow combining portion defines an outer annular passageway surrounding an upper portion of the outlet of the sample chamber and wherein the inlet of the flow combining portion is connected generally tangentially to said outer annular passageway to provide spiral flow of the carrier gas within the flow combining portion.

6. The system of claim 1 having flow passageways extending from the sample chamber, through the flow combining portion and to the analyzing device that are disposed in a substantially straight path for providing a substantially straight obstruction free path for a sample passing between the sample chamber and the analyzing device.

* * * * *